United States Patent [19]

Groebler

[11] Patent Number: 4,786,170
[45] Date of Patent: Nov. 22, 1988

[54] APPARATUS FOR THE GRAPHIC REPRESENTATION AND ANALYSIS OF FLUORESCENCE SIGNALS

[75] Inventor: Bernhard Groebler, Jena-Lobeda, German Democratic Rep.

[73] Assignee: Jenoptik Jena G.m.b.H., Jena, German Democratic Rep.

[21] Appl. No.: 862,734

[22] Filed: May 13, 1986

[30] Foreign Application Priority Data

Jul. 26, 1985 [DD] German Democratic Rep. .................... 2790077

[51] Int. Cl.⁴ .................. G01J 3/443; G01N 21/64
[52] U.S. Cl. .................. 356/318; 356/417; 250/458.1
[58] Field of Search .......... 356/317, 318, 417; 250/458.1, 459.1, 461.1, 461.2, 365

[56] References Cited

U.S. PATENT DOCUMENTS 4,031,398  6/1977  Callis et al. ............... 250/365
4,461,572  7/1984  Tsuchiya ................... 356/318
4,631,581  12/1986  Carlsson ................... 356/318
4,632,550  12/1986  Hara et al. ................ 356/317

Primary Examiner—F. L. Evans
Attorney, Agent, or Firm—Jordan and Hamburg

[57] ABSTRACT

An apparatus for the graphic representation and analysis of fluorescence signals that can be employed for the analysis of the decay behavior of pulses in fluorometry. The object of providing an arrangement for quantitative fluorometry, with which images of the spatial distribution of the decay behavior in microobjects in the nanosecond range can be generated and displayed, is accomplished by producing the fluorescence pulse, for example by pulsed laser light, and processing the pulse further in its totality or in parts thereof rapidly reacting electronic devices. The fluorescence energy can be deposited in memory elements and be used for the pictorial representation. The object is moved in grid fashion by an electronic control arrangement and the process can be repeated as often as desired.

9 Claims, 2 Drawing Sheets

APPARATUS FOR THE GRAPHIC REPRESENTATION AND ANALYSIS OF FLUORESCENCE SIGNALS

BACKGROUND OF THE INVENTION

The invention may be employed for the graphic representation and analysis of fluorescence signals, especially for the decay behavior of such signals, which can be used, for example, to investigate the bonding of dyes to substances in biological cells.

Equipment is known for the fluorescence analysis of microobjects, for which the whole of the object constantly encounters the beam of exciting radiation. With this equipment, an image of the object structure, which normally is viewed with eyepieces or which also can be investigated photometrically, is outlined by means of the fluorescence radiation emanating from the object. These solutions of the problem have the disadvantage that the fluorescence intensity decreases during the investigation and that consecutively measured values are not directly comparable. The possibility of a short-time analysis of the fluorescence process exists (Beyer, H., Hanbush de Mikroskopie (Handbook of Microscopy), Berlin, 1977). a short-time analysis is necessary when the objects to be investigated emit fluorescing radiation, which cannot be separated adequately by wavelength-dispersive means from the fluorescing radiation of the surroundings, as described in the German Patent No. 2,818,841.

Equipment is furthermore known for the short-time fluorescence analysis of the smallest object sites, for which an extremely short light pulse is focussed through a microobjective onto the sample and the variation with time of the fluorescence pulse emanating from the irradiated object site is recorded by means of fast photoelectric receivers and subsequently shown graphically and/or analyzed mathematically, as described by Docchio, F., et al., in Journ. Microsc. 134 (1984) 151. This equipment is free of so-called fading and offers the possibility of timeresolved fluorometry. In principle, it is admittedly possible with this equipment to obtain through repeated application an overview of the spatial distribution of substances with a timewise different fluorescence response, but only if much time is expended on the procedure.

To eliminate this difficulty, the proposal is made in the German Patent No. 3,037,983 C2 to use a receiver diode array in the scanning direction in the focal plane of a scanning microscope. This ensures again only a slight time resolution and can be used only with relatively slowly decaying fluorescence and therefore not with most of the important natural fluorescences of biological cells or with other normal fluorochromes.

Admittedly, the solution to the problem described in the U.S. Pat. No. 4,284,897 largely limits fading; however, it contains no means for analyzing the fluorescence process as a function of time.

SUMMARY OF THE INVENTION

It is an object of the invention to provide an arrangement for quantitative fluorometry, with which the disadvantages of the state of the art are minimized and time is saved.

The object of the invention is the provision of an arrangement for quantitative fluorometry, with which it is possible to produce images of the spatial distribution of the fluorescence decay behavior in microobjects in the nanosecond range and to provide a form of representation for the spatial distribution of this decay behavior, which enables the images to be obtained rapidly and emphasizes certain object details on the basis of the characteristic pulses or with which constant changes in the pulses can be shown as a function of location in a manner clearly interpretable.

This objective is accomplished by an apparatus for the graphic representation and analysis of fluorescence signals owing to the fact that the pulse of exciting radiation, advantageously emanating from a laser, can be focused through an objective onto the sample and that this sample can be shifted by suitable means, for example, in conformity with a grid. The fluorescing light emanating from the irradiated location on the sample is recorded by rapidly reacting photoelectric equipment. Said equipment may contain electronic gate circuits, coincidence devices or a streak camera, with which the whole of the fluorescing pulse or time-limited parts thereof can be processed further and said parts can be fixed by the choice of the times of their beginning and end.

Moreover, the energy of the fluorescing pulse or of one or several of said parts or parameters derived therefrom can be stored as numerical values or as suitable physical quantities in memory elements, which are allocated to the irradiated spot of the sample and that the course of the measurement, so described, can be repeated for an assemblage of points of the object field that is to be examined, for example, in conformity with a grid, so that finally the pictorial representation of certain timewise different fluorescences of the sample field becomes possible.

Said time-limited fluorescence pulse portions are so selected and/or linked in such a manner with arithmetic and/or logic operators, that object points, the fluorescence of which has a special decay behavior, are emphasized on the pictorial representation. A special type of said linkage may exist therein that the energy values of the fluorescence pulses or parts thereof can be utilized to control the primary colors of a color monitor.

The signal-to-noise ratio is affected in an advantageous manner by repeating the whole process several times and continuously averaging the values in the memory elements.

BRIEF FIGURE DESCRIPTION

The invention will now be explained in greater detail with reference to the drawings, wherein.

DISCLOSURE OF PREFERRED EMBODIMENT

Figure 1:
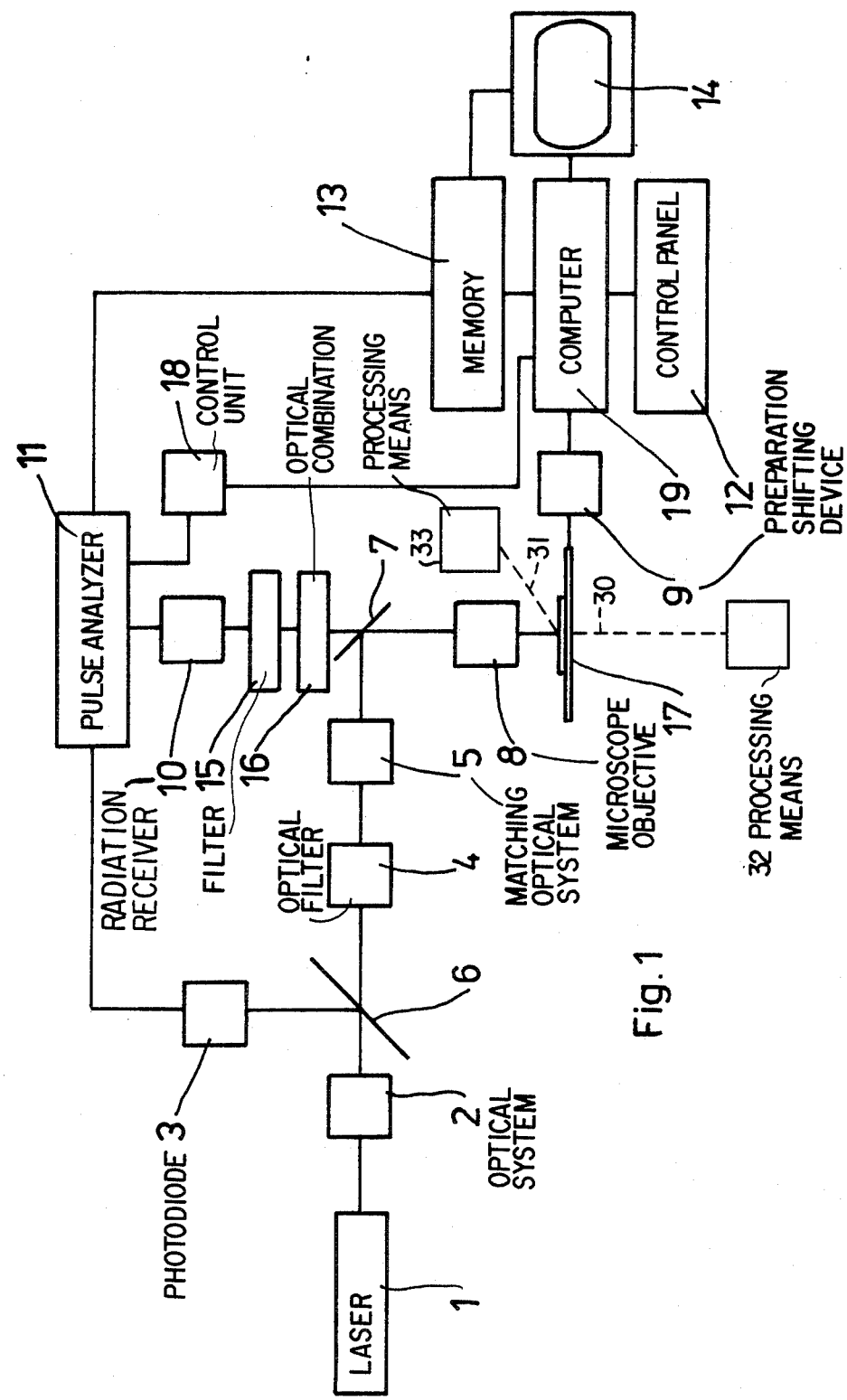
FIG. 1 shows the schematic construction of the arrangement.

In FIG. 1, a laser 1 emits a sequence of short light pulses, the wave length of which is suitable for stimulating the fluorescence in objects of the preparation 17. The pulses pass through a matching optical system 2, the beam divider 6, the filter 4 and the matching optical system 5, the beam divider 7 and the microscope objective 8 and reach the preparation 17, which is in the focal plane of the microscope objective 8. The object parts of the preparation 17, struck by the pulses, emit corresponding fluorescing pulses which, after the microscope objective 8, travel through the beam divider 7, an optical combination 16 and a filter 15 and strike a rapidly reacting radiation receiver 10. The electrical pulses, triggered at the radiation receiver 10, are supplied to a pulse analyzer 11. Moreover, the pulse analyzer 11 also receives electric pulses from the fast photodiode 3, which receives a portion of each exciting pulse from the beam divider 6.

The pulse analyzer 11 can be adjusted, by its operating elements, by computer 19 with its control panel 12 and the counting and control unit 18, to various modes of operation, which permit either the energy of the total fluorescence pulse or the energy of one or several time sections of this pulse to be processed further. The beginning and end of the respective pulse portion can be selected by adjustable time intervals, which elapse from the arrival of the electrical pulse from the photodiode 3 up to the desired time.

The pulse analyzer 11 may also be so adjusted that the energy portions, which are to be processed further and which correspond to a selectable, but constantly the same number of consecutive exciting pulses, are averaged before they are processed further.

The fluorescence energy portions belonging to a preparation pixel, whether averaged or not, are deposited as numerical values in one or several elements of the memory 13, which is or are allocated to the pixel. Depending on the operating regime selected, the preparation 17 is then shifted by one step by the preparation shifting device 9 that is controlled by the computer 19, when one or always the same number of consecutive fluorescence signals has been evaluated for a pixel.

The magnitude and direction of the steps to be carried out by preparation 17 can be controlled as desired by the computer 19 and is accomplished advantageously according to a grid. The whole of the object field of the preparation 17 is thus evaluated as desired and the corresponding fluorescence energy values are deposited in the memory 13.

Figure 2:
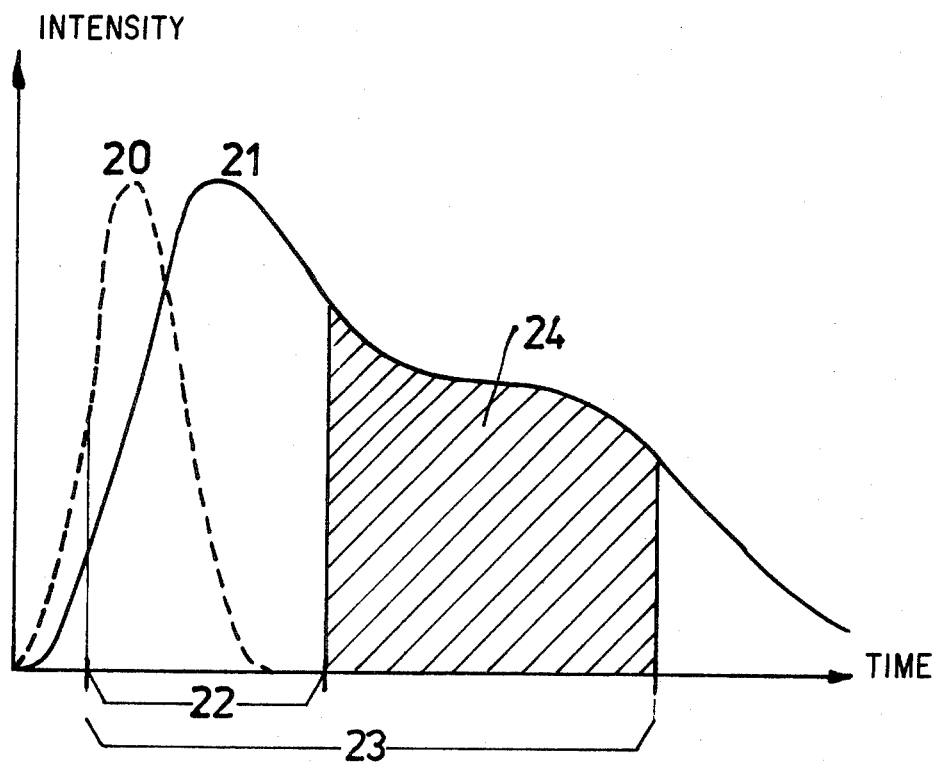
FIG. 2 shows the courses of the exciting and fluorescing pulses.

Parallel or subsequently to this process, the contents of the memory 13 are presented pictorially on the display 14. The mode of operation of the pulse analyzer 11, the computer 19, the memory 13 and the display 14 enables an image of the preparation part examined to be depicted alternately according to the total energy of the fluorescence pulses or according to the time-dependent energy portions or according to mathematical connections of the same. In particular, the energy portions or their connections on the display 14 can be used for pseudocoloring the image. FIG. 2 (shows) a possible case of the course of the exciting pulse 20, which is represented by the electrical pulse from the photodiode and of the fluorescence pulse 21, as well as of one of the pulse portions 24, which commences later than the exciting pulse 20 by the time interval 22 and ends later than the exciting pulse 20 by the time interval 23.

As illustrated in FIG. 1, light 30 passing through the preparation 17, and/or light 31 scattered from the preparation 17, may be processed by any conventional means 32, 33.

I claim:

1. In an apparatus for the graphic representation and quantitative analysis of fluorescence signals, comprising a source of exciting light for exciting a preparation to fluoresce and photoelectric means for analyzing and recording the resulting fluorescing pulses, wherein the preparation can be shifted relative to the exciting light, the improvement comprising means for presenting at least one time-limited portion of a fluorescing pulse for further processing, means for fixing the timelimited portions by the selection of the times of starting and ending each portion, means for storing a quantity corresponding to the energy of at least one of said fluorescing pulses in elements of an image memory, wherein the memory elements are allocated in pairs to the irradiated preparation sites, and wherein all the desired sites of the preparation are evaluable by shifting the preparation, and means for pictorially representing the contents of the image memory.

2. Arrangement as defined in claim 1, comprising means for similarly evaluating a selectable number of fluorescing pulses, which is the same for all the desired sites of the preparation, and means for designating the sums or average values of the fluorescing energies or portions thereof, corresponding to each site of the preparation, to be processed further.

3. Arrangement as defined in claim 2, comprising a color display for the pictorial representation of the fluorescence energies whereby the stored value serve to pseudocolor the image.

4. Arrangement as defined in claim 3, further comprising, for the purpose of improving the color saturation and the signal-to-noise ratio, means for accumulating the image contributions of the measurement cycles and for showing the accumulated image contributions continuously on the display.

5. Arrangement as defined in claim 3, additionally comprising means for using the fluorescing pulses for further processing.

6. Arrangment as defined in claim 5, additionally comprising means for using the light passing through the preparation and/or scattered by this preparation for further processing.

7. A method for the graphic representation and quantitative analysis of fluorescence signals, in which a preparation is excited to fluoresce by exciting light from a source of light and the resulting fluorescing pulses are analyzed and recorded by a photoelectric device and the preparation can be shifted relative to the exciting light, the improvement comprising presenting a complete fluorescing pulse or time-limited portions thereof for further processing, fixing the time-limited portions by the selection of the times of starting and ending of each portion, storing the complete energy of the fluorescing pulse or the energy of one or several of the time-limited portions thereof or of parameters derived by suitable operations from the energy amounts in elements of an image memory, allocating the memory elements in pairs to the irradiated preparation sites, evaluating all the desired sites of the preparation by shifting the preparation and, finally, subsequently pictorially representing the contents of the image memory.

8. The method as defined in claim 7, comprising similarly evaluating a selectable number of fluorescing pulses, which is the same for all the desired sites of the preparation, and designating the sums or average values of the fluorescing energies or portions thereof, corresponding to each site of the preparation, to be processed further.

9. In an apparatus for the graphic representation and quantitative analysis of fluorescence signals, comprising a source of exciting light for exciting a preparation to flouresce and photoelectric means for analyzing and recording the resulting fluorescing pulses, wherein the preparation can be shifted relative to the exciting light, the improvement comprising means for presenting at least one time-limited portion of a fluorescing pulse for further processing, means for fixing the timelimited portions by the selection of the times of starting and ending each portion, means for storing a quantity corresponding to the energy of at least one of said fluorescing pulses in elements of a display that luminesces for a long time, wherein the elements of the display are allocated in pairs to the irradiated preparation sites, and wherein all the desired sites of the preparation are evaluable through shifting the preparation, said display comprising means for pictorially representing the contents of said elements.

* * * * *